(12) United States Patent
Zhang

(10) Patent No.: US 10,393,660 B2
(45) Date of Patent: Aug. 27, 2019

(54) APPARATUS AND METHOD FOR MEASURING CONCENTRATION OF MATERIALS IN LIQUID OR GAS

(71) Applicant: Jianfeng Zhang, Sugarland, TX (US)

(72) Inventor: Jianfeng Zhang, Sugarland, TX (US)

( * ) Notice: Subject to any disclaimer, the term of this patent is extended or adjusted under 35 U.S.C. 154(b) by 0 days.

(21) Appl. No.: 15/803,815

(22) Filed: Nov. 5, 2017

(65) Prior Publication Data

US 2018/0128746 A1 May 10, 2018

Related U.S. Application Data

(60) Provisional application No. 62/418,225, filed on Nov. 6, 2016.

(51) Int. Cl.
| | |
|---|---|
| *H04N 7/18* | (2006.01) |
| *G01N 21/64* | (2006.01) |
| *G02B 5/20* | (2006.01) |
| *G02B 7/02* | (2006.01) |
| *H04N 5/232* | (2006.01) |
| *G01N 15/14* | (2006.01) |
| *G06T 7/73* | (2017.01) |
| *G01N 21/51* | (2006.01) |

(Continued)

(52) U.S. Cl.
CPC ......... *G01N 21/6456* (2013.01); *G01N 15/06* (2013.01); *G01N 15/1429* (2013.01); *G01N 15/1434* (2013.01); *G01N 21/51* (2013.01); *G02B 5/20* (2013.01); *G02B 7/02* (2013.01); *G06T 7/73* (2017.01); *H04N 5/23245* (2013.01); *G01N 21/532* (2013.01); *G01N 2015/0693* (2013.01); *G02B 5/208* (2013.01); *G06T 2207/10152* (2013.01); *G06T 2207/30242* (2013.01)

(58) Field of Classification Search
CPC .............. G01N 15/06; G01N 21/6456; G01N 15/1429; G01N 15/1434; G01N 2015/0693; G01N 21/51; G01N 21/532; G01N 21/6458; H04N 5/23245; G02B 5/20; G02B 5/208; G02B 7/02; G06T 2207/10152; G06T 2207/30242; G06T 7/73
USPC .......................................... 250/301; 348/135
See application file for complete search history.

(56) References Cited

U.S. PATENT DOCUMENTS

| | | | | |
|---|---|---|---|---|
| 2011/0102790 A1* | 5/2011 | Haught | ..................... | G01J 3/02 356/319 |
| 2013/0235189 A1* | 9/2013 | Thabeth | .................. | B08B 7/028 348/135 |

(Continued)

*Primary Examiner* — Jessica M Prince
(74) *Attorney, Agent, or Firm* — Ingenium Patents LLC; Peter R. Kramer

(57) ABSTRACT

An apparatus and method which measure the concentration of suspended, dispersed or dissolved materials in a fluid. The invention utilizes two light emitters, a light filter or dichroic mirror, a lens and an imaging sensor. The apparatus evaluates the magnitude of the fluorescence light emitted by the materials when excited by a light of suitable wavelength, and uses the magnitude in a correlation to determine the concentration of the materials to be measured. The apparatus further evaluates the magnitude of transmitted or scattered light from another light emitter, which is used through a correlation, in combination with the correlation for the fluorescence magnitude, to determine the concentration of the materials when fluorescence light alone cannot determine the concentration.

38 Claims, 11 Drawing Sheets

Figure 1:
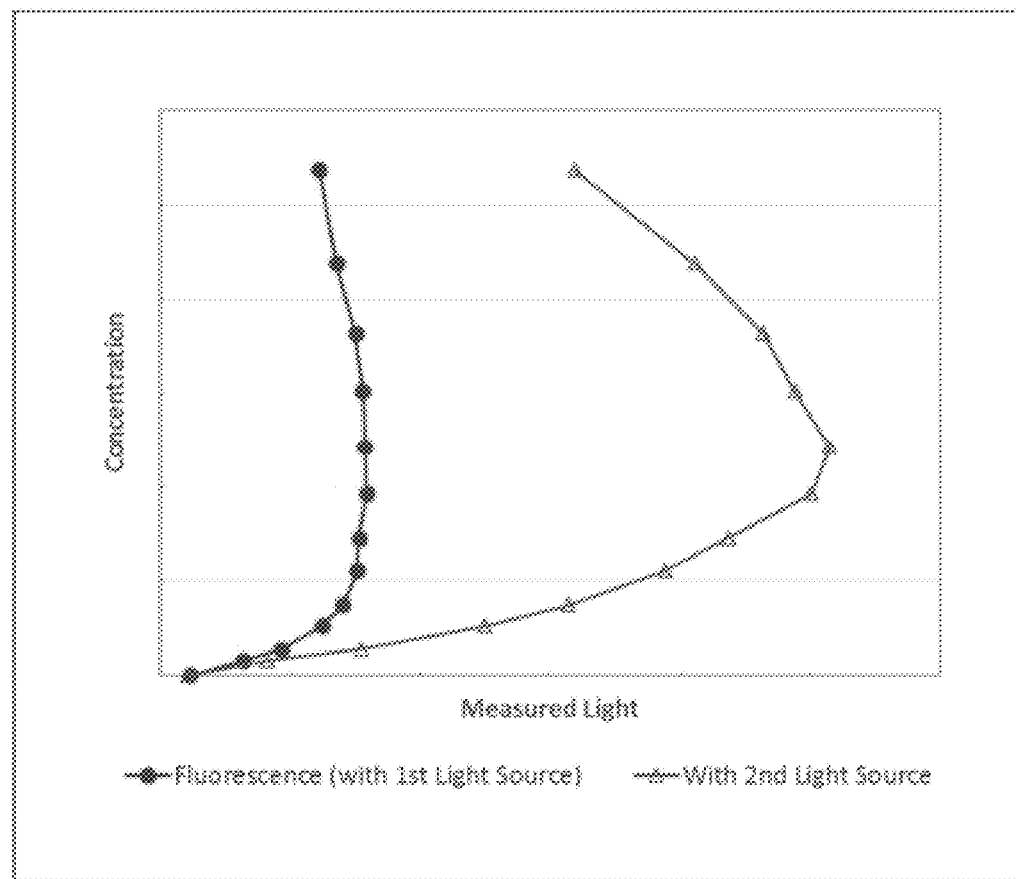

(51) Int. Cl.
*G01N 15/06* (2006.01)
*G01N 21/53* (2006.01)

(56) References Cited

U.S. PATENT DOCUMENTS

2016/0258870 A1* 9/2016 Tokhtuev ............... G01N 33/18
2017/0075099 A1* 3/2017 Fine ....................... G02B 21/34

* cited by examiner

APPARATUS AND METHOD FOR MEASURING CONCENTRATION OF MATERIALS IN LIQUID OR GAS

CROSS-REFERENCE TO RELATED APPLICATIONS

This application claims priority to provisional application No. 62/418,225 filed on 6 Nov. 2016. The contents of provisional application 62/418,225 are hereby incorporated by reference. Claim 26 does not claim priority to provisional application 62/418,225, which claims the embodiment of FIG. 8.

BACKGROUND OF THE INVENTION

Field of the Invention

The field of the invention is apparatus and method for the measurement of fluorescent materials in an aqueous or gaseous fluid. Examples of the application include the measurement of oil in water produced from petroleum and natural gas reservoirs, measurement of oil droplets in flowing natural gas, detection and quantification of oil in ocean or other bodies of water, and measurement of other fluorescent materials in transparent fluids.

Description of Related Art

Various apparatus and methods for measurement of concentrations of materials in liquid and gas, such as the amount of hydrocarbon in water have been described in patents or applications in patents. These are represented by the following: U.S. Pat. Nos. 4,394,573, 5,418,614, 5,489,977, 5,912,459, 6,140,637, 6,255,118, 6,507,401B1, 6,525,325, 7,099,012, 7,470,917, 7,935,938, 8,017,928, US Patent Application 20060246595, US Patent Application 2008/0173804, and US Patent Application 20120061589.

Devices made with the related art have been used with various degree of success. However, some of shortcomings of the related art are that they are either of limited range, for example applicable for less than about 100 ppm of hydrocarbon in water, or expensive in implementation. There are many situations at present where monitoring the trend of concentration is desired but the monitors with the described related art are too costly for the purpose. Therefore there exists the need for low cost apparatuses to monitor the concentration of materials in fluid.

BRIEF SUMMARY OF THE INVENTION

The present invention is an apparatus and method which measure the concentration of suspended, dispersed or dissolved materials in a fluid. The invention utilizes two light emitters, a light filter or dichroic mirror, a lens and an imaging sensor. The apparatus evaluates the magnitude of the fluorescence light emitted by the materials when excited by a light of suitable wavelength, and uses the magnitude in a correlation to determine the concentration of the materials to be measured. The apparatus further evaluates the magnitude of transmitted or scattered light from another light emitter, which is used through a correlation, in combination with the correlation for the fluorescence magnitude, to determine the concentration of the materials when fluorescence light alone cannot determine the concentration. Multiple configurations of the apparatus are possible. The general method is the same for the configurations and the details vary between the configurations.

The present invention combines the use of fluorescence and light absorption principles, with the measurements achieved by switching two light sources on and off alternatively, and record the responses from the fluid to be measured by a camera. With this invention a monitoring device can be built with much lower cost than other monitoring devices while achieving similar measurement concentration range and measurement accuracy. This makes it economically feasible to monitor the fluid in many situations, such as disposal of oil-field produced water and waste-water treatment, where the other devices are too expensive to be used.

BRIEF DESCRIPTION OF THE SEVERAL VIEWS OF THE DRAWING(S)

Figure 2:
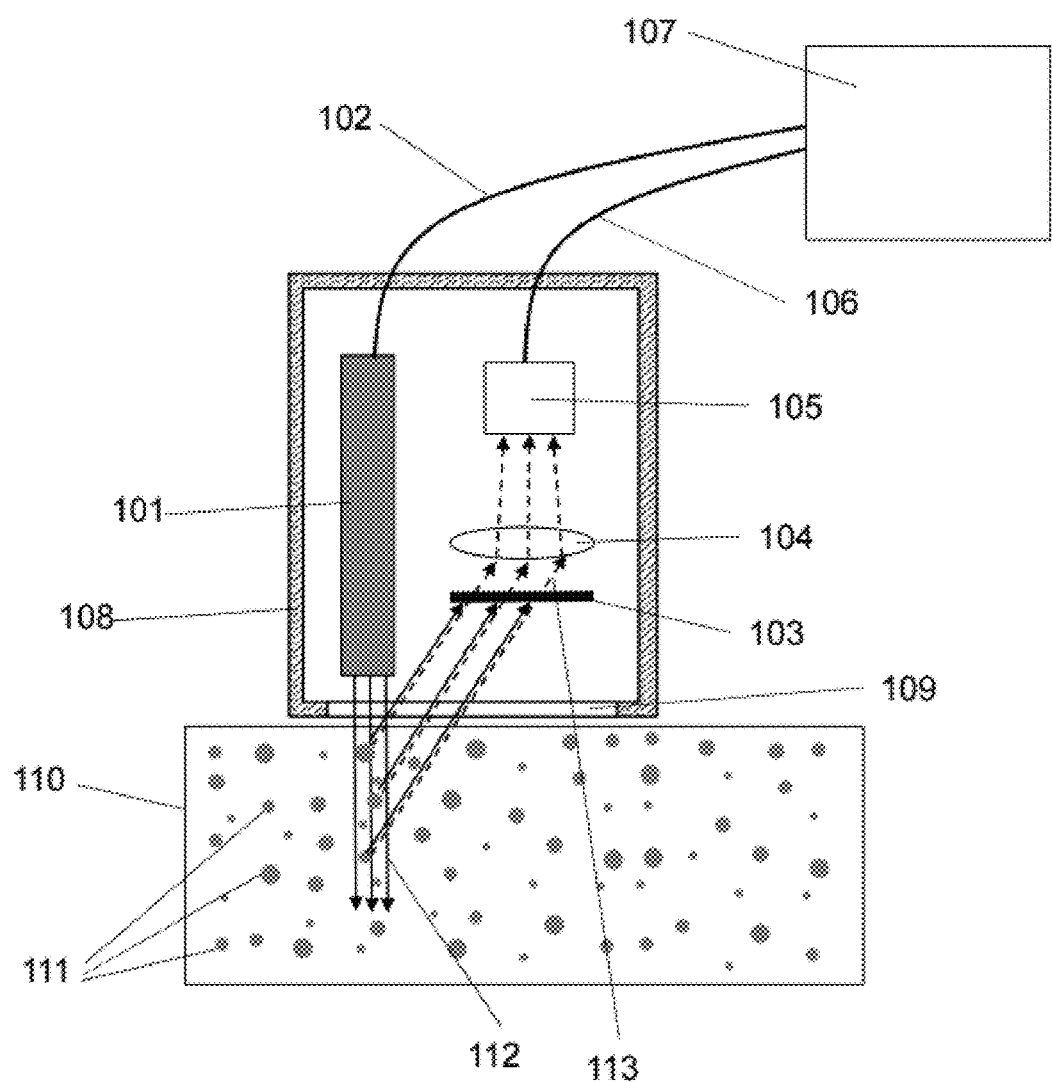
Figure 3:
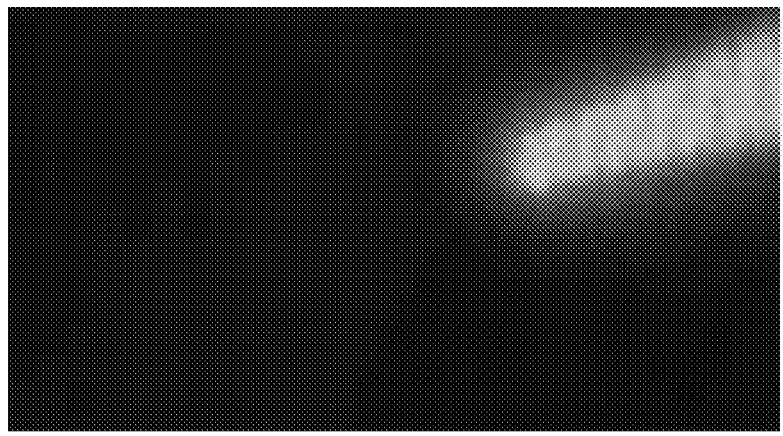

FIG. 1 Concentration vs Measured light with $1^{st}$ light source and $2^{nd}$ light source FIG. 2 Schematic view of Configuration 1 using one light emitter FIG. 3 Image captured using Configuration 1

Figure 4A:
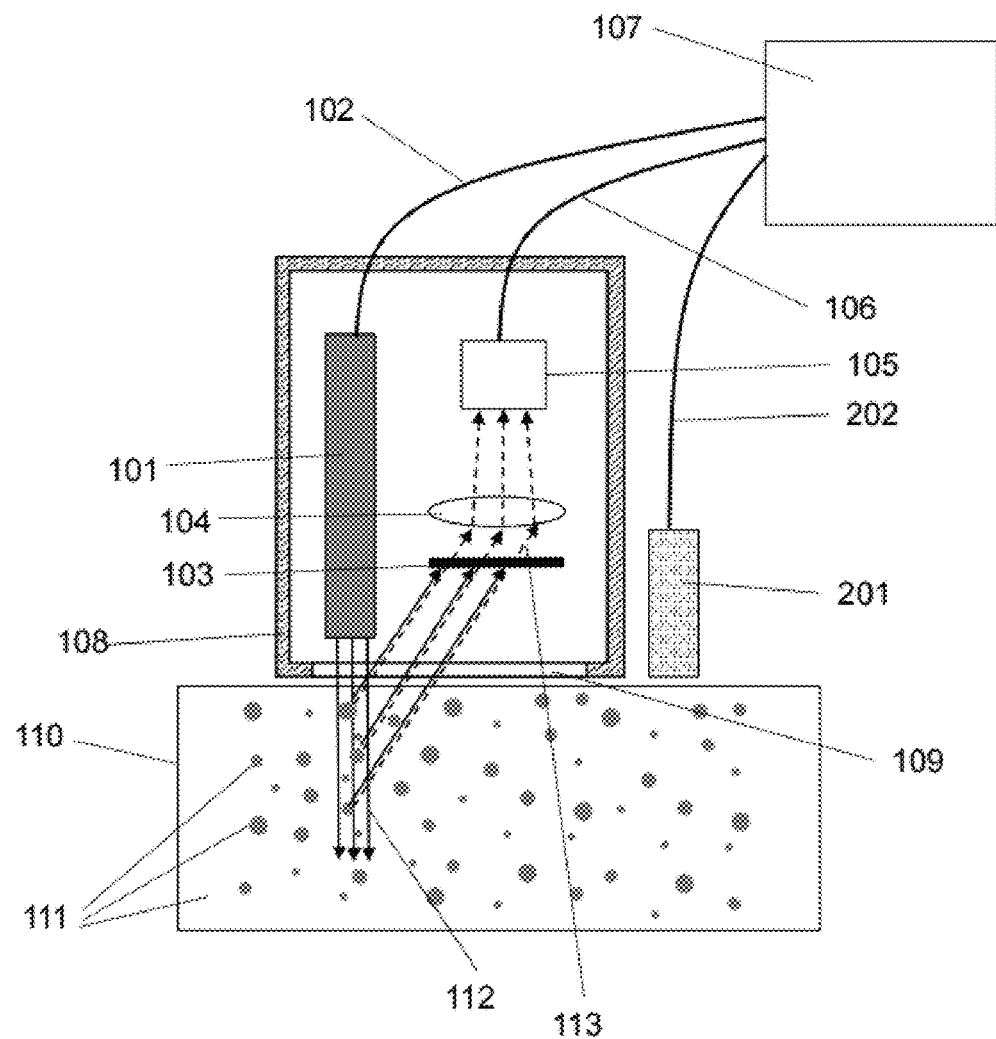
Figure 4B:
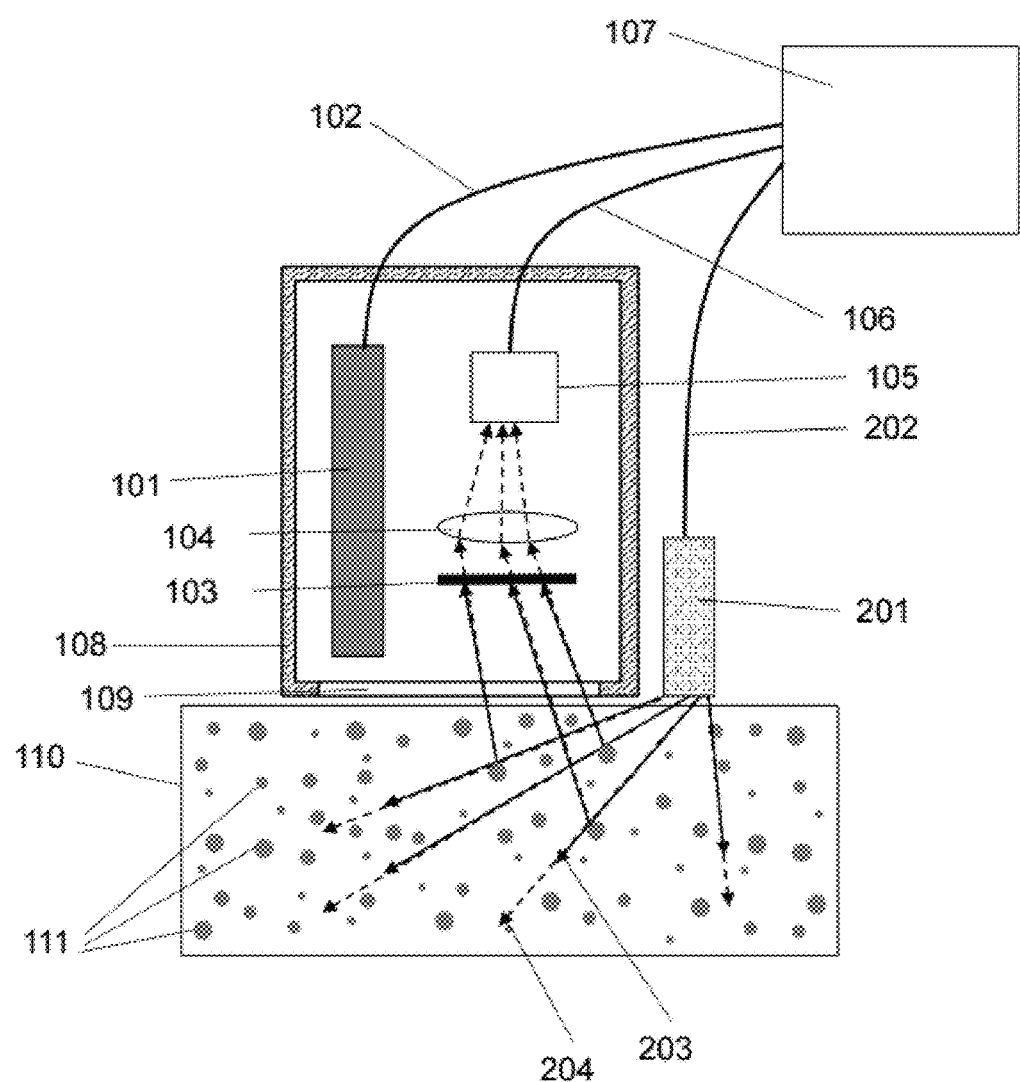
Figure 5:
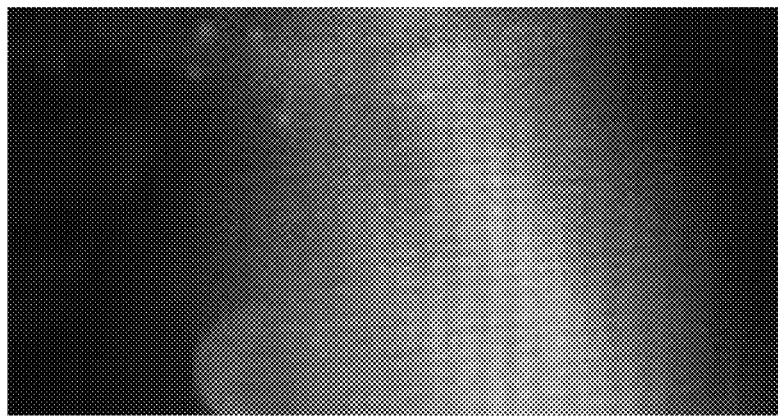

FIG. 4A Schematic view of Configuration 2 with two light emitters, with first light emitter on and second light emitter off FIG. 4B Schematic view of Configuration 2 with two light emitters, with first light emitter off and second light emitter on FIG. 5 Image captured using Configuration 2

Figure 6:
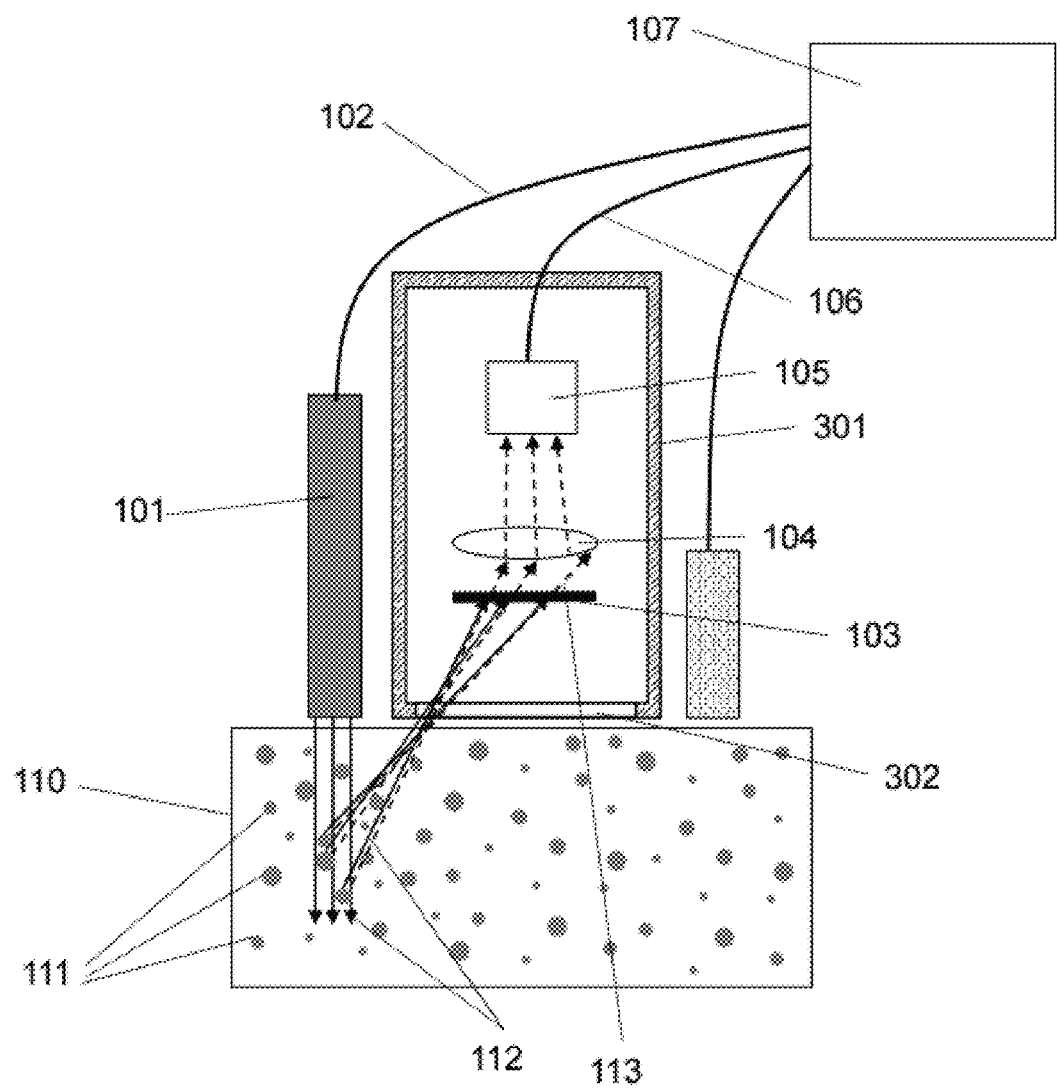
Figure 7:
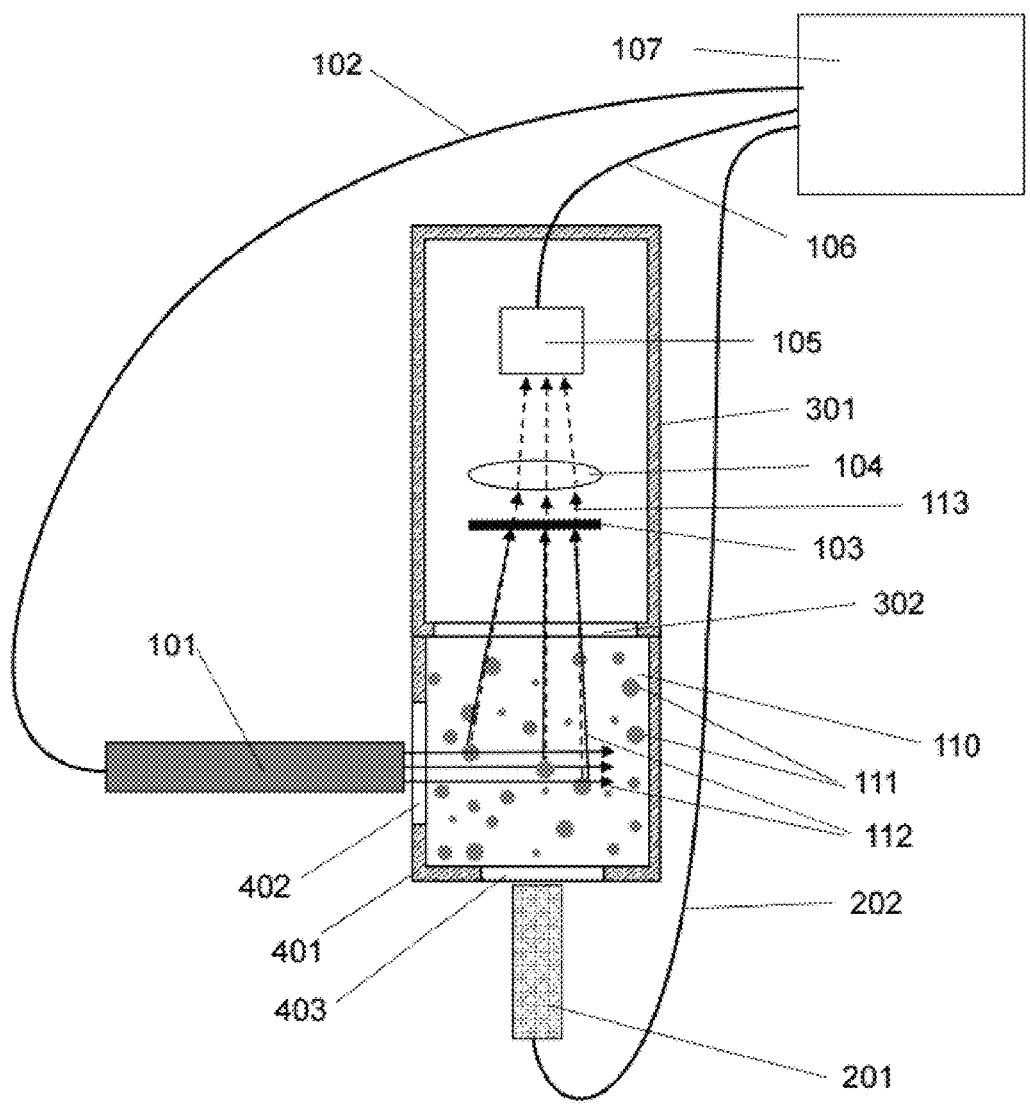
Figure 8:
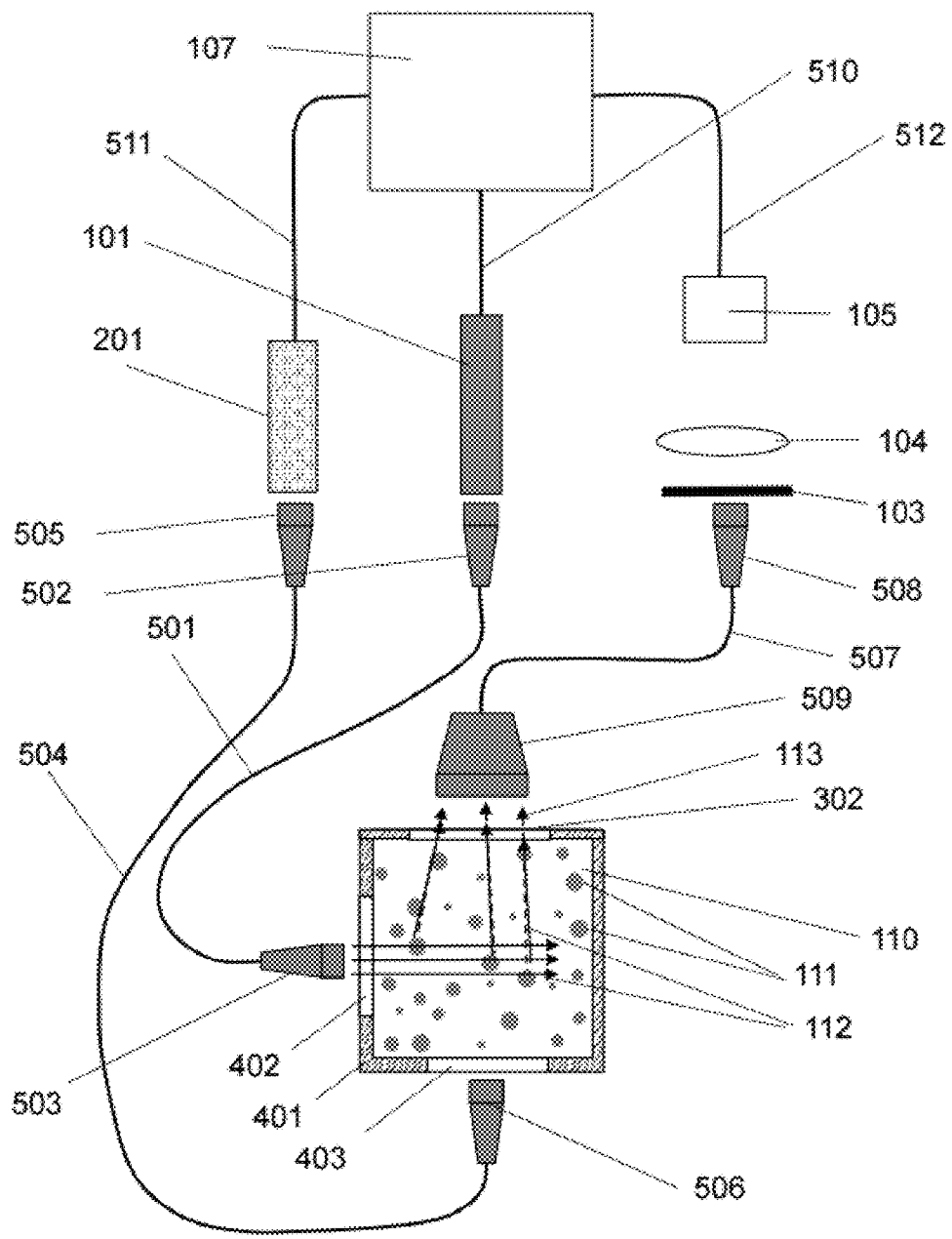
Figure 9:
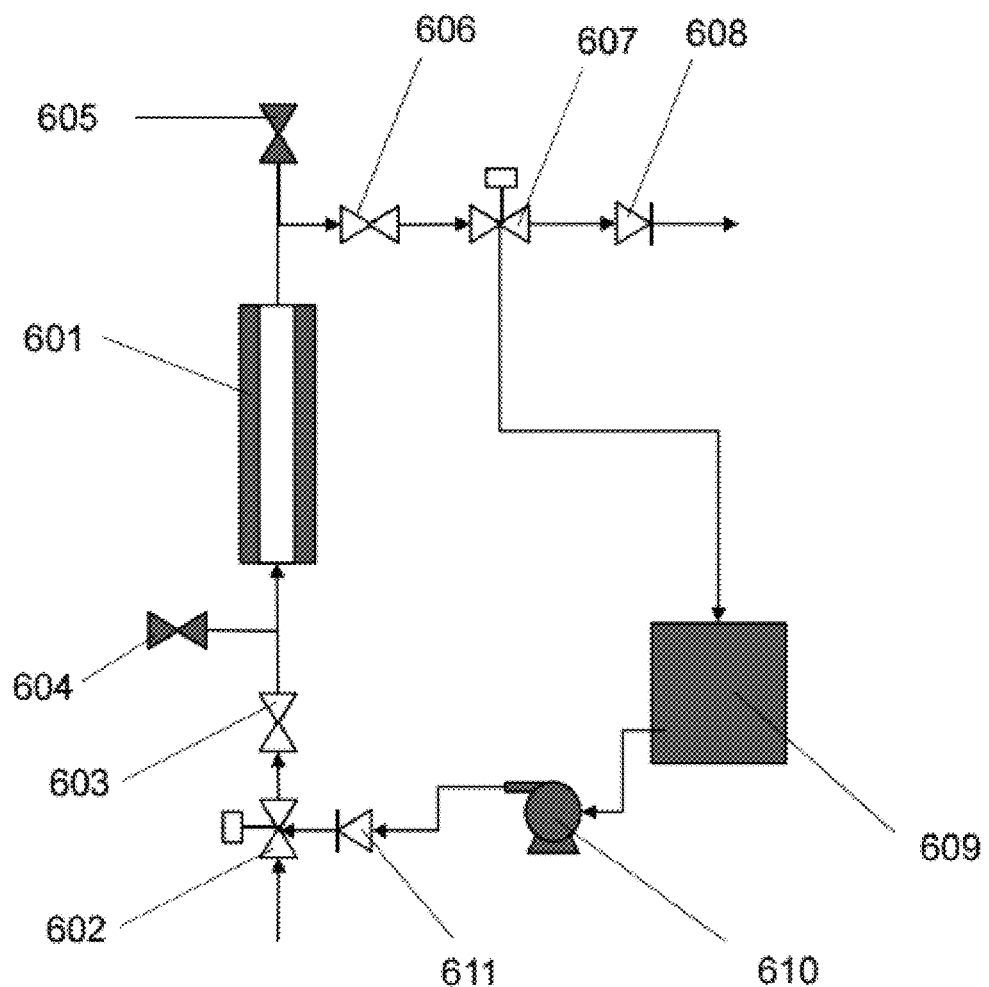
Figure 10:
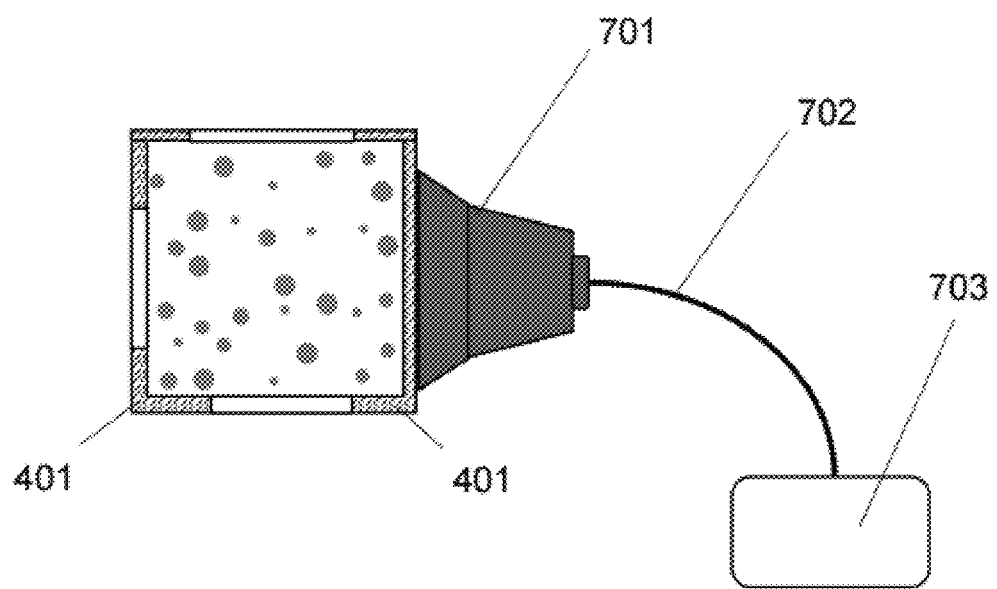

FIG. 6 Schematic view of a variant configuration with both emitters outside the housing for filter, lens, and imaging sensor FIG. 7 Schematic view of another variant configuration with first light emitter positioned side-ways from imaging assembly FIG. 8 Schematic view of another variant configuration with light emitters and imaging assembly positioned at some distance away from the fluid to be measured FIG. 9 A schematic showing an aspect providing for removal of fouling from optical windows FIG. 10 A schematic showing another aspect providing for removal of fouling from optical windows

DETAILED DESCRIPTION OF THE INVENTION

It is known that certain materials emit fluorescent light, or fluorescence, under excitation by a light of suitable wavelength, such as ultraviolet or visible light, and the magnitude can be correlated to the concentration of such materials suspended, dispersed or dissolved in a transparent liquid or gas. In measurement apparatuses utilizing this principle, the fluorescence light is typically separated from the reflected light with a light filter, and the fluorescence light is detected by a photon-multiplier tube (PMT) or a photodiode. The inventors discovered that imaging sensors such as Complementary Metal-Oxide-Semiconductor (CMOS) or Charge-Coupled Device (CCD) can be used to form low cost apparatuses to measure the magnitude of the fluorescent light from which the concentration of the fluorescence materials can be determined. The images acquired from the imaging sensor also enable the assessment of whether the optical window(s) have been fouled, which is another significant benefit since window fouling is a frequent and primary cause for fluorescence-based measurement devices to drift to lower accuracy.

As the concentration of the material increases, the magnitude of fluorescence emission increases monotonically until a certain concentration. Further increase in concentration may lead to plateauing and decreasing of the light magnitude, as illustrated FIG. 1. Therefore, there is an upper limit on the measurable concentration, beyond which value there are two potential concentrations corresponding to each measured fluorescence magnitude, thus disabling the measurement of concentration from fluorescence alone.

The inventors discovered that using an additional light emitter, the upper limit on the measurable concentration can be significantly increased. The second light emitter emits broad-spectrum light or light at a wavelength that can go through the filter or be reflected by the dichroic mirror, and reach the imaging sensor. As illustrated FIG. 1, the strength of this light measured by the imaging sensor also initially increases with the concentration of the materials to be measured, then plateaus and decreases with further increase of concentration. Since the quantitative relationships between the measured light and concentration are different between the two light emitters, the two magnitudes can be used together to determine the concentration, expanding the range of measurable concentration to much larger than that with fluorescence only.

Configuration 1: One Light Emitter

One preferred configuration of the apparatus and method is to use fluorescence only. The configuration is illustrated in FIG. 2, where:

101 is an emitter of light with a single wavelength in the range from ultraviolet to visible light. A particularly preferred emitter is a laser generator. Another particularly preferred emitter is a single-color light emitting diode (LED). In a variation, emitter 101 can also be outside the housing 108.

102 is a group of wires connecting laser emitter 101 to a controller 107.

103 is a long-pass optical filter that blocks the light with the same wavelength as the light from emitter 101, but allows the fluorescence light emitted by the materials to be measured (111) to pass through.

104 is a lens for focusing the light onto the imaging sensor 105.

105 is an imaging sensor. Two preferred types of the imaging sensor are CMOS and CCD.

106 is a group of wires connecting the imaging sensor 105 to controller 107.

107 is a controller that provides power to the light emitter 101, initiates and stops the emission of light from emitter 101, provides power to sensor 105, and processes the images from 105 to produce the measurement values on the concentration of the materials to be measured (111). Controller 107 also includes a computer for controller functions and analysis of the images.

108 is a housing for the emitter 101, optical components 103 and 104, and imaging sensor 105.

109 is an optical aperture for the emitted light, the reflected light, and fluorescence emissions from the materials to be measured to pass through.

110 is a body of stationary or moving fluid which contains a primary component, such as water or gas, which does not fluoresce under light excitation, and secondary components that fluoresce under light excitation. The assembly of housing 108, aperture 109 and the internals can be outside 110 as shown. 110 can be contained in a pipe or container, and an optical window between 110 and 109 provides the path for light. Variations including the assembly is fully or partially submerged in 110.

111 is the collection of secondary components, such as oil droplets or dissolved oil, which fluoresce under light excitation and are the material to be measured. The materials can be suspended or dispersed as illustrated, or dissolved.

112 (shown in solid arrows) are the light emitted from emitter 101, and light reflected by the fluorescent materials 111.

113 (shown in dashed arrows) are the fluorescence emitted by the materials to be measured, 111, under the excitation of light 112.

To perform a measurement, controller 107 provides power to light emitter 101 on pre-selected duration and frequency. The light 112 from emitter 101 is transmitted to the fluid mixture 110 and reaches some of the fluorescent materials 111. Both the reflected light and the fluorescence reach filter 103, which blocks the reflected light 112 and allows the fluorescence to pass through. Lens 104 focuses the fluorescence light to imaging sensor 105 which captures the images. FIG. 3 shows one example of such images.

The images are electronically transmitted to controller 107, which calculates the total light magnitude from each image by summing the light magnitude of each pixel in the image. The total light magnitude is used to calculate the concentration of the material to be measured. Each measurement cycle can be with one image, or with multiple images for averaging the total light magnitude.

Optionally, an image is also taken by imaging sensor 105 without light emission from light emitter 101. The image is analyzed by controller 107 to obtain the total strength of light captured by imaging sensor 105. This establishes the magnitude of the background light that passes through filter 103. The difference between the total light magnitudes when light emitter 101 is on and off is used to calculate the concentration of the material to be measured.

Multiple variations of the imaging assembly is possible utilizing the same principle for measurements. In one variation, filter 103 is replaced with a dichroic mirror which reflects only the fluorescent light and light with longer wavelength, and allow the light with shorter wavelength light to pass through, and the lens and imaging sensor are positioned on the reflection side of the mirror to acquire images.

Configuration 2: Two Light Emitters

Another preferred configuration of the apparatus and method is to use two light emitters, one for inducing fluorescence from the materials to be measured as described in Configuration 1, and another light emitter providing light with wavelength that is the same as or longer than the fluorescence. The configuration is illustrated in FIGS. 4A and 4B. The components that are the same as in FIG. 1 are labelled the same. The new components for this configuration are:

201 is an emitter of broad-spectrum light, such as a white LED, or an emitter of light with a single wavelength that is the same or longer than the fluorescence light 113.

202 is a group of wires connecting light emitter 201 to controller 107.

203 is the part of the light emitted by 201 which is in the range of wavelength blocked by filter 103.

204 is the part of the light emitted by 201 which is in the range of wavelength allowed to pass through filter 103.

To perform a measurement, the same steps as described for Configuration 1 are first performed, as illustrated in FIG. 4A. In addition, as illustrated by FIG. 4B, emitter 101 is turned off, emitter 201 is turned on for an amount of time specified by controller 107, and one or more images are taken by imaging sensor 105. One example of such images is shown in FIG. 5. The images are analyzed by controller 107 to determine the average strength of light detected by imaging sensor 105. The light strengths measured with emitter 101 on and with emitter 201 on are used in combination to determine the concentration of the material to be measured.

Similar to that for Configuration 1, optionally images can be taken with both emitters 101 and 201 turned off, and the images are analyzed for the strength of the background light which are also used in the calculation of the concentration of the materials to be measured.

Similar to that for Configuration 1, variations of the configuration includes replacing filter 103 with a dichroic mirror which reflects only the fluorescent light and light with longer wavelength and the lens and imaging sensor are positioned on the reflection side of the mirror.

Variations of the Configurations

The configuration can be varied for different applications without changing the principles of the invention.

FIG. 6 shows one potential variation, where the emitters are both outside the housing for the filter, lens and imaging sensor (the imaging assembly), where the components different from those shown in FIG. 2, FIG. 4A and FIG. 4B are:

301 is a housing similar to 108 in FIG. 1 except for smaller, since it does not house the light emitter 101.

302 is an optical aperture similar to 109 in FIG. 1 except for smaller.

FIG. 7 shows another potential variation, where light emitter 101 is positioned side-ways from the imaging assembly and light emitter 201 is positioned directly across the imaging assembly, where the components different from those shown in FIG. 2, FIG. 4A, FIG. 4B and FIG. 6 are:

401 is a conduit or container for the mixture 110.

402 is an optical aperture for the light emitted by 101.

403 is an optical aperture for the light emitted by 201.

FIG. 8 shows another potential variation, where light emitters 101 and 201, and the imaging assembly (103, 104 and 105) are positioned at some distance away from the location of the fluid to be measured, and not in direct line of sight from the fluid. 101, 201, 103, 104 and 105 are optically coupled with the fluid through fiber optic light guides. The components in this configuration that are different from those shown in FIG. 2, FIG. 4A, FIG. 4B, FIG. 6 and FIG. 7 are:

501 is a fiber optical light guide with suitable ends, for transmitting the light from emitter 101 to the fluid, for generating fluorescence from the fluid.

502 is an end termination assembly at one end of light guide 501 to optically couple with light emitter 101. The assembly can be configured in a number of ways, to enhance light transmission such as with polishing of the optical fiber ends, condition the light beam into 501 and out of 501 with built-in lenses or sets of lens, control the spectrum range of the light with an optical filter, a combination of these configurations, as well as other configurations.

503 is an end termination assembly at the other end of light guide 501 to optically couple with the fluid to be measured (housed in the volume formed by 401, 402, 403, and 302). Similar to end termination assembly 502, the assembly can be configured in a number of ways.

504 is a fiber optical light guide for transmitting with suitable ends, the light from emitter 201 to the fluid, for the light to go through the fluid.

505 and 506 are end terminations assemblies for fiber optic light guide 504. They can be configured with similar features as 502 and 503, but with potentially different specifics on the lens, filter and other components to be suitable for the light transmitted by emitter 201.

507 is a fiber optical light guide with suitable ends, for collecting the fluorescence generated by the fluid, light scattered by the fluid, and light transmitted through the fluid to the imaging assembly.

508 and 509 are end termination assemblies for fiber optic light guide 507. They can be configured with similar features as 502, 503, 505 and 506, but with potentially different specifics on the lens, filter and other components to be suitable for the light from the measured fluid in response to the light transmitted to the fluid from light emitters 101 and 201. Assemblies 508 and 509 may also have different specifics in configuration so that they are each best suited for its intended functions of collecting light or sending the light to the imaging assembly.

510, 511, and 512 are respectively groups of electrical wires connecting the light emitters 101, 201, and imaging sensor 105 to controller 107.

Cleaning of Optical Windows

One of the important aspects for obtaining accurate measurements on the concentrations of materials in fluid with optical methods such as described herein is to keep the fouling on the optical windows at a sufficiently low level. FIG. 9 shows an approach for removal of fouling from the optical windows with circulation of cleaning fluid and optional manual access. FIG. 10 shows another approach, which uses ultrasonic cleaning transducer or transducers attached near the optical windows.

In FIG. 9:

601 is the measurement section in simplified elevation view. It is the combination of 401, 402 and 403 described in plan views in FIGS. 7 and 8.

The arrows refer to the direction of flow.

602 is a three-way valve, or an assembly of two-way valves and pipe fittings to achieve switching of flow direction. It can be an actuated valve or set of valves, or can be manual valves.

603, 604, 605, and 606 are two-way valves. 604 and 605 can also be plugs for the opening to the fluid conduit between valves 603 and 606.

607 is a three-way valve similar to 602.

608 is a check valve which permits flow in only one direction as shown by the arrows.

609 is a container for cleaning fluid that is used for removing fouling. The cleaning fluid is a liquid that can be clean water, the fluid from the stream to be measured, or other suitable liquid, plus optionally additives such as surfactant, detergent, acid and other chemicals that are needed for removing the fouling.

610 is a pump for circulating the cleaning fluid. The pump can be in line as shown or submerged in the cleaning fluid in container 609.

611 is a check valve which permits flow in only one direction as shown by the arrows.

During normal measurement operation, the fluid to be measured flows into 602 from the direction shown by the arrow below 602, passes through valves 603, measurement section 601, valves 606, 607 and 608, and exit in the direction shown by the arrow to the right of 608. Valves 604 and 605 are closed. Pump 610 is not operational.

To active the fouling removal mechanism, valves 602 and 607 switch to the other direction, for the flow path of cleaning fluid to be open. Pump 610 operates and circulate the cleaning fluid to measurement section 601 and back to container 609. At the end of the fouling removal operation, pump 610 is stopped and valves 602 and 607 are switched to the directions as in normal measurement operation.

To remove fouling by manual access to measurement section 601, valves 603 and 606 are closed, and valve 605 is open. A suitable cleaning fluid can be poured through 605 into 601. Additionally, a brush, liquid jetting nozzle, or other devices can be inserted through 605 for cleaning.

Manual access to 601 can be through 605 for inspecting the optical windows for cleanness with a suitable device such as a bore imaging camera.

Fluid can be poured into 601 through 605 for confirming the optical windows are cleaned to within specification, calibration, or both.

In FIG. 10:

401 is the conduit or container of the fluid to be measured, same as described in FIG. 7.

701 is an ultrasonic cleaning transducer, attached to an area of 401 that is close to the optical windows.

702 is a group of electrical wires.

703 is an electrical driver device

To remove fouling, 701 is activated by driver 703 for a suitable period of time.

Fouling Removal Operation:

The fouling removal mechanisms can be activated by direct human operations on the device, by automated triggering, or combination of both. The activation timing can be at selected by a number of ways, including with pre-selected intervals, with fouling is detected.

Detection and Assessment of Fouling:

One advantage of the dual imaging operation described by this invention is that the two types of images can be combined to detect the presence of fouling and the extent of fouling. Examples of the methods to use the images for detection and assessment of fouling are:

The relationship of the magnitudes of the light recorded by the two types of images are compared with that when the optical windows are known to be clean, and the deviations as evaluated, A series of images recorded when light source 201 is switched on are analyzed for patterns to identify either general reduction of brightness, or presence areas that are consistently darker than the rest of the image, as time of operation progresses.

The presence of the deviations and the image patterns would indicate possibility of fouling, and the final determination can be achieved when other factors are included, such as whether there are operational changes that can affect the characteristics of the incoming fluid.

Evaluation after Fouling Removal:

After the fouling removal operation has been carried out, the images can be used in the similar manner on the restarted flow of the fluid to be measured, to evaluate whether fouling has been removed to a satisfactory level for the normal measurement operation to resume, or whether further fouling removal is still needed.

It will be appreciated that those skilled in the art will be able to devise numerous alternative arrangements that, while not shown or described herein, embody the principles of the invention and thus are within its spirit and scope.

I claim:

1. An apparatus for determining the concentration of suspended, dispersed or dissolved materials in a liquid or gas, comprising,
   a) a container to hold the materials, a first aperture, and a second aperture, said container having said first aperture and said second aperture,
   b) a first light emitter which emits light at ultraviolet or visible light wavelengths through said first aperture, that can induce fluorescence from the material to be measured, having a first on or off(non) light emitting switch,
   c) a second light emitter which emits light through said second aperture, that contains wavelengths that are the same as or longer than the said fluorescence, having a second on or off(non) emitting light switch,
   d) either a common filter or a dichroic mirror which separates said fluorescence from light of the same wavelength as light from said first light emitter,
   e) a lens focusing separated fluoresced light,
   f) a sensor for creating and capturing images with the light focused by said lens,
   g) an integrated, a partly, or fully remote controller which operates said first and second light emitter switches, and performs image acquisition functions at various operation modes of the first and second light emitter switches, compares and analyzes the images, and calculates the concentration of said materials to be measured.

2. The apparatus in claim 1, wherein said first light emitter is a laser emitting device.

3. The apparatus in claim 1, wherein said first light emitter is a light emitting diode.

4. The apparatus in claim 1, wherein said first light emitter is a lamp.

5. The apparatus of claim 2 wherein said sensor for creating images is a CMOS device.

6. The apparatus of claim 5 configured wherein said first light emitter switch is in an on-emitting state and said second light emitter is in an off-non-emitting state.

7. The apparatus of claim 5 configured wherein said second light emitter switch is in an on-emitting state and said first light emitter is in an off-non-emitting state.

8. The apparatus of claim 2 wherein said sensor for creating images is a CCD device.

9. The apparatus of claim 8 configured wherein said first light emitter is in an on-emitting state and said second light emitter is in an off-non-emitting state.

10. The apparatus of claim 8 configured wherein said second light emitter is in an on-emitting state and said first light emitter is in an off-non-emitting state.

11. The apparatus of claim 3 wherein said sensor for creating images is a CMOS device.

12. The apparatus of claim 11 configured wherein said first light emitter is in an on-emitting state and said second light emitter is in an off-non-emitting state.

13. The apparatus of claim 11 configured wherein said second light emitter is in an on-emitting state and said first light emitter is in an off-non-emitting state.

14. The apparatus of claim 3 wherein said sensor for creating images is a CCD device.

15. The apparatus of claim 14 configured wherein said first light emitter is in an on-emitting state and said second light emitter is in an off-non-emitting state.

16. The apparatus of claim 14 configured wherein said second light emitter is in an on-emitting state and said first light emitter is in an off-non-emitting state.

17. The apparatus of claim 4 wherein said sensor for creating images is a CMOS device.

18. The apparatus of claim 17 configured wherein said first light emitter is in an on-emitting state and said second light emitter is in an off-non-emitting state.

19. The apparatus of claim 17 configured wherein said second light emitter is in an on-emitting state and said first light emitter is in an off-non-emitting state.

20. The apparatus of claim 4 wherein said sensor for creating images is a CCD device.

21. The apparatus of claim 20 configured wherein said first light emitter is in an on-emitting state and said second light emitter is in an off-non-emitting state.

22. The apparatus of claim 20 configured wherein said second light emitter is in an on-emitting state and said first light emitter is in an off-non-emitting state.

23. A method of measuring the concentration of suspended, dissolved or dissolved materials in a liquid or gas mixture, comprising the following steps:
   a) illuminating the mixture of said materials to be measured wherein the liquid or gas is illuminated by light from a first light emitter, wherein said first light emitter emits light at ultraviolet or visible light wavelengths that can induce fluorescence from the material to be measured,
   b) capturing at least one fluorescence-only first image with an imaging sensor,
   c) calculating the total light magnitude or the average of light magnitudes from the image with light from said first light emitter,
   d) illuminating said mixture with light from a second light emitter, wherein light from said second light emitter is comprised of wavelengths that are the same as or longer than the said fluorescence,
   e) capturing at least one second image with said imaging sensor using light from said second light emitter,
   f) the total light magnitude or the average of light magnitudes are calculated from said images with light from said second light emitter,
   g) calculating the concentration of said material to be measured using total light magnitudes from said illumination by said first light emitter and from said illumination by said second light emitter.

24. The method in claim 23, further comprising wherein:
   a) one or more non-illuminated images are taken without illumination by light from said first light emitter or said second light emitter,
   b) calculating total light magnitude of said images using the magnitudes of the light from images acquired from steps b) and e) from claim 23, to calculate the concentration of said material to be measured.

25. A method of measuring the concentration of suspended, dissolved or dissolved materials in a liquid or gas mixture, comprising the following steps:
   a) illuminating the mixture of said materials to be measured wherein the liquid or gas is illuminated by light from a light emitter,
   b) capturing at least one fluorescence-only image with an imaging sensor, wherein said light emitter emits light at ultraviolet or visible light wavelengths that can induce fluorescence from the material to be measured
   c) calculating the total light magnitude or the average of light magnitudes from the image with light from said light emitter,
   d) calculating the concentration of said material to be measured using total light magnitudes from said illumination by said light emitter.

26. The apparatus according to claim 1 further comprising wherein said first and second light emitters and said filter, said lens, and said sensor, said filter lens and sensor collectively comprising an imaging assembly, are positioned such that they are not in direct line of sight from the liquid or gas, and said apparatus is further configured with fiber optic guides wherein said first and second light emitters, said fiber optic guides each having end termination assemblies at a receiving end which receives light from each respective emitter, and each fiber optic guide having a transmitting end that optically couples to the fluid, said apparatus further comprising wherein said imaging assembly, said first light emitter and second light emitter are electrically connected to the controller.

27. The apparatus of claim 1, further comprising,
   a pump, valves, and fluid lines,
   said valves and fluid lines arranged to permit entry and exit of fluid to be measured into a measurement section, said measurement section comprised of said container, said first aperture, and said second aperture, and said valves and fluid lines further arranged to permit exit of said fluid to be measured from the apparatus,
   said valves and fluid lines further arranged to permit introduction of a cleaning fluid into said measurement section and to permit efflux of cleaning solution from said apparatus,
   said apparatus further configured to detect fouling by measuring magnitudes of light recorded by the two types of images, determining a current relationship of said magnitudes, and comparing said current relationship to a control relationship determined under conditions wherein the optical windows are clean,
   wherein said relationship comprises either a general reduction of brightness or presence of areas that are consistently darkened within the image.

28. The apparatus of claim 5, further comprising,
   a pump, valves, and fluid lines,
   said valves and fluid lines arranged to permit entry and exit of fluid to be measured into a measurement section, said measurement section comprised of said container, said first aperture, and said second aperture, and said valves and fluid lines further arranged to permit exit of said fluid to be measured from the apparatus,
   said valves and fluid lines further arranged to permit introduction of a cleaning fluid into said measurement section and to permit efflux of cleaning solution from said apparatus,
   said apparatus further configured to detect fouling by measuring magnitudes of light recorded by the two types of images, determining a current relationship of said magnitudes, and comparing said current relationship to a control relationship determined under conditions wherein the optical windows are clean,
   wherein said relationship comprises either a general reduction of brightness or presence of areas that are consistently darkened within the image.

29. The apparatus of claim 8, further comprising, a pump, valves, and fluid lines,
   said valves and fluid lines arranged to permit entry and exit of fluid to be measured into a measurement section, said measurement section comprised of said container, said first aperture, and said second aperture, and said valves and fluid lines further arranged to permit exit of said fluid to be measured from the apparatus,
   said valves and fluid lines further arranged to permit introduction of a cleaning fluid into said measurement section and to permit efflux of cleaning solution from said apparatus,
   said apparatus further configured to detect fouling by measuring magnitudes of light recorded by the two types of images, determining a current relationship of said magnitudes, and comparing said current relationship to a control relationship determined under conditions wherein the optical windows are clean, wherein said relationship comprises either a general reduction of brightness or presence of areas that are consistently darkened within the image.

30. The apparatus of claim 11, further comprising, a pump, valves, and fluid lines, said valves and fluid lines arranged to permit entry and exit of fluid to be measured into a measurement section, said measurement section comprised of said container, said first aperture, and said second aperture, and said valves and fluid lines further arranged to permit exit of said fluid to be measured from the apparatus, said valves and fluid lines further arranged to permit introduction of a cleaning fluid into said measurement section and to permit efflux of cleaning solution from said apparatus, said apparatus further configured to detect fouling by measuring magnitudes of light recorded by the two types of images, determining a current relationship of said magnitudes, and comparing said current relationship to a control relationship determined under conditions wherein the optical windows are clean, wherein said relationship comprises either a general reduction of brightness or presence of areas that are consistently darkened within the image.

31. The apparatus of claim 14, further comprising, a pump, valves, and fluid lines, said valves and fluid lines arranged to permit entry and exit of fluid to be measured into a measurement section, said measurement section comprised of said container, said first aperture, and said second aperture, and said valves and fluid lines further arranged to permit exit of said fluid to be measured from the apparatus, said valves and fluid lines further arranged to permit introduction of a cleaning fluid into said measurement section and to permit efflux of cleaning solution from said apparatus, said apparatus further configured to detect fouling by measuring magnitudes of light recorded by the two types of images, determining a current relationship of said magnitudes, and comparing said current relationship to a control relationship determined under conditions wherein the optical windows are clean, wherein said relationship comprises either a general reduction of brightness or presence of areas that are consistently darkened within the image.

32. The apparatus of claim 17, further comprising, a pump, valves, and fluid lines, said valves and fluid lines arranged to permit entry and exit of fluid to be measured into a measurement section, said measurement section comprised of said container, said first aperture, and said second aperture, and said valves and fluid lines further arranged to permit exit of said fluid to be measured from the apparatus, said valves and fluid lines further arranged to permit introduction of a cleaning fluid into said measurement section and to permit efflux of cleaning solution from said apparatus, said apparatus further configured to detect fouling by measuring magnitudes of light recorded by the two types of images, determining a current relationship of said magnitudes, and comparing said current relationship to a control relationship determined under conditions wherein the optical windows are clean, wherein said relationship comprises either a general reduction of brightness or presence of areas that are consistently darkened within the image.

33. The apparatus of claim 27 further comprising, a cleaning fluid container, an ultrasonic cleaning transducer, an electrical driver device, electrical connection between said ultrasonic cleaning transducer and said electrical driver device.

34. The apparatus of claim 28 further comprising, a cleaning fluid container, an ultrasonic cleaning transducer, an electrical driver device, electrical connection between said ultrasonic cleaning transducer and said electrical driver device.

35. The apparatus of claim 29 further comprising, a cleaning fluid container, an ultrasonic cleaning transducer, an electrical driver device, electrical connection between said ultrasonic cleaning transducer and said electrical driver device.

36. The apparatus of claim 30 further comprising, a cleaning fluid container, an ultrasonic cleaning transducer, an electrical driver device, electrical connection between said ultrasonic cleaning transducer and said electrical driver device.

37. The apparatus of claim 31 further comprising, a cleaning fluid container, an ultrasonic cleaning transducer, an electrical driver device, electrical connection between said ultrasonic cleaning transducer and said electrical driver device.

38. The apparatus of claim 32 further comprising, a cleaning fluid container, an ultrasonic cleaning transducer, an electrical driver device, electrical connection between said ultrasonic cleaning transducer and said electrical driver device.

* * * * *

UNITED STATES PATENT AND TRADEMARK OFFICE
CERTIFICATE OF CORRECTION

PATENT NO. : 10,393,660 B2
APPLICATION NO. : 15/803815
DATED : August 27, 2019
INVENTOR(S) : Zhang et al.

Page 1 of 1

It is certified that error appears in the above-identified patent and that said Letters Patent is hereby corrected as shown below:

On the Title Page

At Item (72), Inventors: At line two add the following names:
Stuart Baskin, Katy, TX (US);
Zetong Gu, Chicago, IL (US)

Signed and Sealed this
Fifth Day of May, 2020

Andrei Iancu
*Director of the United States Patent and Trademark Office*